(12) United States Patent
Wong et al.

(10) Patent No.: US 9,303,289 B2
(45) Date of Patent: *Apr. 5, 2016

(54) PHASED GENOME SEQUENCING

(71) Applicant: The Board of Trustees of the Leland Stanford Junior University, Stanford, CA (US)

(72) Inventors: Wing H. Wong, Stanford, CA (US); Hong Yang, San Mateo, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 4 days.

This patent is subject to a terminal disclaimer.

(21) Appl. No.: 14/330,707

(22) Filed: Jul. 14, 2014

(65) Prior Publication Data

US 2015/0011409 A1 Jan. 8, 2015

Related U.S. Application Data

(63) Continuation of application No. 13/297,062, filed on Nov. 15, 2011, now Pat. No. 8,778,638.

(60) Provisional application No. 61/422,000, filed on Dec. 10, 2010.

(51) Int. Cl.
C12Q 1/68 (2006.01)

(52) U.S. Cl.
CPC ............ *C12Q 1/6869* (2013.01); *C12Q 1/6804* (2013.01)

(58) Field of Classification Search
CPC ........... C12Q 1/6869; C12Q 2537/164; C12Q 2565/626; C12Q 1/6804
USPC .......................................................... 435/6.1
See application file for complete search history.

(56) References Cited

U.S. PATENT DOCUMENTS

| | | | |
|---|---|---|---|
| 8,778,638 B2 * | 7/2014 | Wong et al. ................... | 435/91.2 |
| 8,785,127 B2 * | 7/2014 | Drmanac ....................... | 435/6.11 |
| 2005/0053986 A1 | 3/2005 | Makarov et al. | |
| 2010/0099092 A1 | 4/2010 | Song et al. | |
| 2010/0105052 A1 | 4/2010 | Drmanac et al. | |
| 2010/0273658 A1 | 10/2010 | Feinberg et al. | |
| 2011/0033862 A1 | 2/2011 | Rabinowitz et al. | |
| 2012/0010085 A1 | 1/2012 | Rava et al. | |

OTHER PUBLICATIONS

Brock et al. (1999) "Densely methylated sequences that are preferentially localized at telomere-proximal regions of human chromosomes" *Gene* 240(2):269-277.
Carrano et al. (1979) "Measurement and purification of human chromosomes by flow cytometry and sorting" *Proc Natl Acad Sci USA* 76(3):1382-1384.
Chen et al. (2009) "Long-range linkage on chromosome 6p of VEGF, FKBP5, HLA and TNF alleles associated with transplant rejection" *Mol Immunol* 47(1):96-100.
Chial (2008) "Cytogenetic Methods and Disease: Flow Cytometry, CGH and FISH" *Nature Education* 1(1):1-4.
Fantes & Green (1990) "Human chromosome analysis and sorting" *Methods Mol Biol* 5:529-542.
Hayashizaki et al. (1994) "Identification of an imprinted U2af binding protein related sequence on mouse chromosome 11 using the RLGS method" *Nat Genet* 6(1):33-40.
Huang et al. (1999) "Methylation profiling of CpG islands in human breast cancer cells" *Hum Mol Genet* 8(3):459-470.
Kleinjan & Van Heyningen (2005) "Long-range control of gene expression: emerging mechanisms and disruption in disease" *Am J Hum Genet* 76(1):8-32.
Kong et al. (2009) "Parental origin of sequence variants associated with complex diseases" *Nature* 462(7275):868-874.
Levy et al. (2007) "The diploid genome sequence of an individual human" *PLoS Biol* 5, e254.
Montgomery et al. (2010) "Transcriptome genetics using second generation sequencing in a Caucasian population" *Nature* 464(7289):773-777.
Murphy et al. (2005) "Sequencing of genomic DNA by combined amplification and cycle sequencing reaction" *Clin Chem* 51(1):35-39.
Nunome et al. (2010) "Detection of recombinant haplotypes in wild mice (*Mus musculus*) provides new insights into the origin of Japanese mice" *Mol Ecol* 19(12):2474-2489.
Pickrell et al. (2010) "Understanding mechanisms underlying human gene expression variation with RNA sequencing" *Nature* 464(7289):768-772.
Plass et al. (1996) "Identification of Grf1 on mouse chromosome 9 as an imprinted gene by RLGS-M" *Nat Genet* 14(1):106-109.
Pritchard et al. (2010) "The genetics of human adaptation: hard sweeps, soft sweeps, and polygenic adaptation" *Curr Biol* 20(4):R208-215.
Sabeti et al. (2002) "Detecting recent positive selection in the human genome from haplotype structure" *Nature* 419(6909):832-837.
Shiraishi (1999) "Isolation of DNA fragments associated with methylated CpG islands in human adenocarcinomas of the lung using a methylated DNA binding column and denaturing gradient gel electrophoresis" *Proc Natl Acad Sci USA* 96(6):2913-2918.
Stein (2008) "Next-Generation Sequencing Update: With the Advent of Sophisticated Platforms, Genomes Can Be Sequenced in Record Time" *Genetic Engineering & Biotechnology News* 28(15) 5 pgs.
Toyota et al. (1999) "Identification of differentially methylated sequences in colorectal cancer by methylated CpG island amplification" *Cancer Res* 59(10):2307-2312.
Winkler et al. (2010) "Admixture mapping comes of age" *Annu Rev Genomics Hum Genet* 11:65-89.

\* cited by examiner

*Primary Examiner* — Cynthia B Wilder
(74) *Attorney, Agent, or Firm* — Edward J. Baba; Shweta Chandra; Bozicevic, Field & Francis LLP

(57) ABSTRACT

The present disclosure provides methods for determining phased nucleic acid sequence for a single chromosome of interest and/or a single chromosomal fragment of interest. The present disclosure also provides methods for determining phased nucleic acid sequence for a plurality of single chromosomes of interest and/or a plurality of single chromosomal fragments of interest. The plurality of single chromosomes of interest may be of one chromosome type or of two or more chromosome types. The present disclosure also provides a method for isolating a plurality of chromosomal fragments of a specified size range, where the chromosomal fragments are from one or more specified regions of the genome. The plurality of chromosomal fragments may be separated into single chromosomal fragments and sequenced to provide phased nucleic acid sequence for the single chromosomal fragments. Alternatively, the plurality of chromosomal fragments may be sequenced together to provide unphased nucleic acid sequence for the chromosomal fragments.

12 Claims, 7 Drawing Sheets

PHASED GENOME SEQUENCING

CROSS-REFERENCE TO RELATED APPLICATIONS

This application is a continuation of U.S. patent application Ser. No. 13/297,062, filed on Nov. 15, 2011, now U.S. Pat. No. 8,778,638, which application claims the benefit of U.S. Provisional Application No. 61/422,000, filed on Dec. 10, 2010, which are herein incorporated by reference in their entirety.

GOVERNMENT RIGHTS

This invention was made with government support under grant nos. R01HG004634 and R01HG003903 awarded by National Institutes of Health. The United States Government has certain rights in this invention.

INTRODUCTION

The two haploid genome sequences that a person inherited from the two parents represent the most fundamentally useful type of genetic information for the study of heritable diseases and the development of personalized medicine. Because of the difficulty in obtaining long-range phase information, current sequencing methods are unable to provide this information.

High-density single nucleotide polymorphism (SNP) arrays can measure the genotypes for millions of SNPs across the genome. However, these genotypes are not phased. Most of the methods designed so far are for haplotyping only a small number of markers. SNP array profiling after chromosome microdissection has also been developed.

There is a need for a method for long-range phase information. The present invention addresses these needs, as well as others.

SUMMARY

The present disclosure provides methods for determining phased nucleic acid sequence for a single chromosome of interest and/or a single chromosomal fragment of interest. The present disclosure also provides methods for determining phased nucleic acid sequence for a plurality of single chromosomes of interest and/or a plurality of single chromosomal fragments of interest. The plurality of single chromosomes of interest may be of one chromosome type or of two or more chromosome types.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 4 A shows that probes that align in vicinity of each other provide a FRET signal. FIG. 4 B shows that probes that do not align in vicinity of each other do not provide a FRET signal.

DETAILED DESCRIPTION OF THE INVENTION

Figure 1:
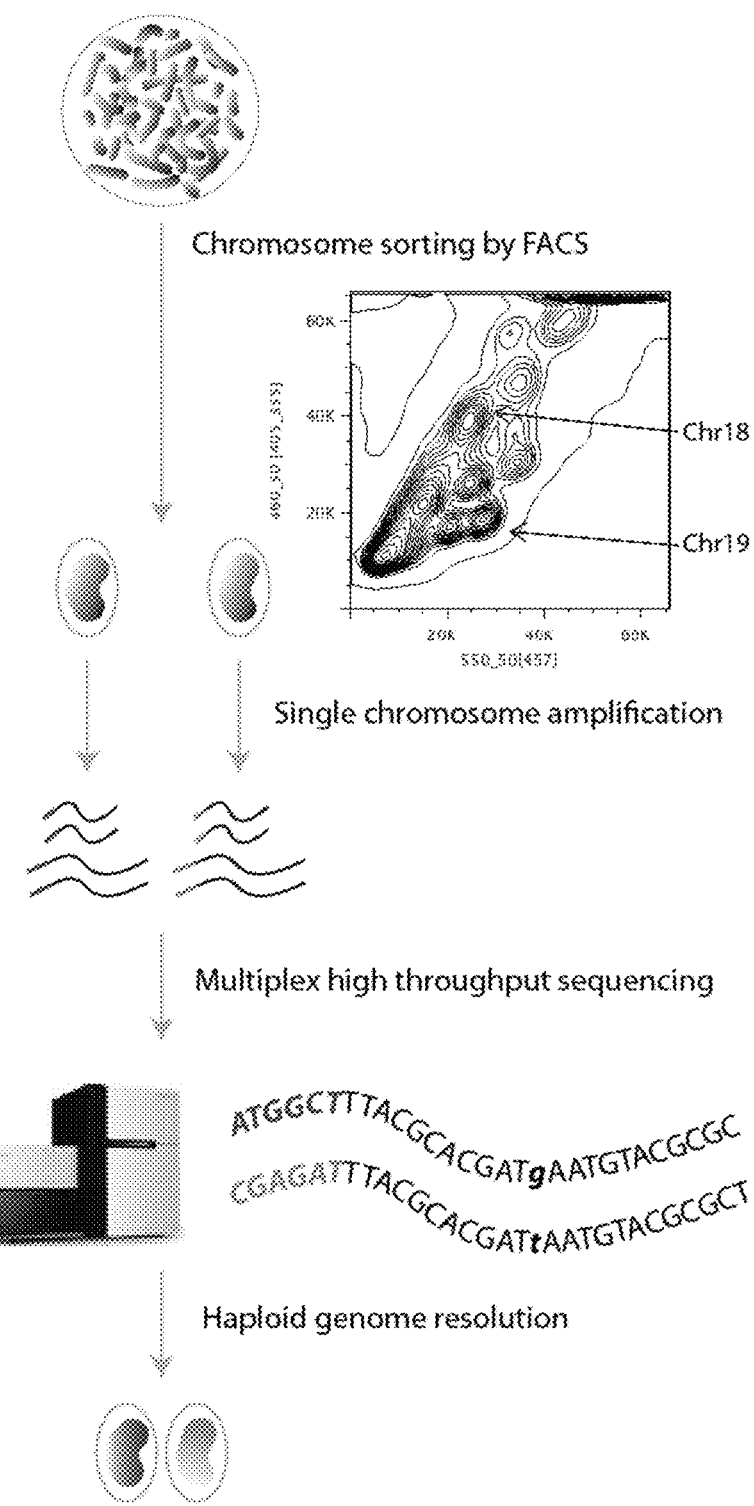
FIG. 1 provides a schematic diagram of Phase-Seq work flow (top sequence: SEQ ID NO:01; bottom sequence: SEQ ID NO:02).

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the exemplary methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a molecule" includes a plurality of such molecules and reference to "the molecule" includes reference to one or more molecules and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

"Oligonucleotide tag" means an oligonucleotide that is attached to a polynucleotide and is used to identify and/or track the polynucleotide in a reaction. Usually, an oligonucleotide tag is attached to the 3'- or 5'-end of a polynucleotide to form a linear conjugate, sometime referred to herein as a "tagged polynucleotide" or equivalently, an "oligonucleotide tag-polynucleotide conjugate," or "tag-polynucleotide conjugate." Oligonucleotide tags may vary widely in size and compositions. The oligonucleotide tags can each have a length within a range of from 4 to 36 nucleotides, or from 6 to 30 nucleotides, or from 8 to 25 nucleotides, for example about 35 nucleotides, 30 nucleotides, 25 nucleotides. In one aspect, oligonucleotide tags are used in sets wherein oligonucleotide tags of each set has a unique nucleotide sequence.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art.

As used herein the term "isolated" is meant to describe a compound of interest (e.g., either a polynucleotide or a polypeptide) that is in an environment different from that in which the compound naturally occurs.

"Purified" as used herein refers to a compound removed from an environment in which it was produced and is at least 60% free, preferably 75% free, and most preferably 90% free from other components with which it is naturally associated or with which it was otherwise associated with during production.

The term "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes.

Perfect complementarity or 100% complementarity refers to the situation in which each nucleotide unit of one polynucleotide strand can hydrogen bond with a nucleotide unit of a second polynucleotide strand, without a "mismatch". Less than perfect complementarity refers to the situation in which not all nucleotide units of two strands can hydrogen bond with each other. For example, for two 20-mers, if only two base pairs on each strand can hydrogen bond with each other, the polynucleotide strands exhibit 10% complementarity. In the same example, if 18 base pairs on each strand can hydrogen bond with each other, the polynucleotide strands exhibit 90% complementarity. Substantial complementarity refers to about 79%, about 80%, about 85%, about 90%, about 95%, or greater complementarity. Thus, for example, two polynucleotides of 29 nucleotide units each, wherein each comprises a di-dT at the 3' terminus such that the duplex region spans 27 bases, and wherein 27 of the 27 bases of the duplex region on each strand are complementary, are substantially complementary. In determining complementarity, overhang regions are excluded.

The term "polynucleotide" or "nucleic acid" refers to polymers of nucleotides of any length, and includes but is not limited to single stranded or double stranded molecule of DNA, RNA, or DNA/RNA hybrids including polynucleotide chains of regularly and irregularly alternating deoxyribosyl moieties and ribosyl moieties (i.e., wherein alternate nucleotide units have an —OH, then and —H, then an —OH, then an —H, and so on at the 2' position of a sugar moiety), and modifications of these kinds of polynucleotides wherein the substitution or attachment of various entities or moieties to the nucleotide units at any position, as well as naturally-occurring or non-naturally occurring backbones, are included. A polynucleotide may be further modified after polymerization, such as by conjugation with a labeling component. A "fragment" or "segment" of a nucleic acid is a small piece of that nucleic acid.

"Homozygous" state means a genetic condition existing when identical alleles reside at corresponding loci on homologous chromosomes. In contrast, "heterozygous" state means a genetic condition existing when different alleles reside at corresponding loci on homologous chromosomes.

A "gene" refers to a polynucleotide containing at least one open reading frame that is capable of encoding a particular protein after being transcribed and translated.

A "subject," "individual" or "patient" is used interchangeably herein, which refers to a vertebrate, e.g., a mammal, e.g., a human.

The term "amplifying" as used herein refers to generating one or more copies of a target nucleic acid, using the target nucleic acid as a template.

The term "probe," as used herein, refers to a nucleic acid that is complementary to a nucleotide sequence of interest.

As used herein, the term "genome(s)" means the hereditary information of an individual typically encoded in nucleic acids, either DNA, or RNA, and including both genes and non-coding sequences. The genome may refer to the nucleic acids making up one set of chromosomes of an organism (haploid genome) or both sets of chromosomes of an organism (diploid genome) depending on the context in which it is used.

A "target chromosome pair" as used herein refers to a pair of chromosomes of the same type, where a member of the pair is maternally inherited (inherited from the mother) and the other member of the pair is paternally inherited (inherited from the father). For example, a target chromosome pair refers to a pair of chromosome 1, chromosome 2, chromosome 3, and including up to chromosome 21, chromosome 22, and chromosome X. One or more target chromosome pairs may be simultaneously analyzed by the methods disclosed herein to determine the sequence of the maternally and paternally inherited chromosome of the target chromosome pair.

A "single copy" or "single copies" of a target chromosome pairs as used herein refers to a single physical DNA molecule, either the chromosome per se, or packaged (with the assistance of chromosomal proteins such as histones) in the form of a chromosome. In a normal diploid human cell, there are 46 single chromosomes, 23 single chromosomes from the mother and 23 single chromosomes from the father. Single copies of a target chromosome are also referred to as single copies of a chromosome type. Single copies of one or multiple chromosome types are usually separated into individual containers in the method described herein.

A "chromosome type" as used herein refers to a specific chromosome present in a cell. In a normal diploid human cell of a female, there are 22 types of autosomal chromosomes and one type of sex chromosome (chromosome X). In a normal diploid human cell of a male, there are 22 types of autosomal chromosomes and two types of sex chromosomes (chromosomes X and Y).

The term "polymorphic site" or "polymorphism" as used herein refers to a localized region within a chromosome at which the nucleotide sequence varies from a reference sequence in at least one individual in a population. Sequence variations can be substitutions, insertions or deletions of one or more bases.

As used herein, the term "single nucleotide polymorphism(s) or SNP(s)" means a polymorphic site at which the sequence variation is caused by substitution of a single base at a specific position. SNPs refer to nucleotide variations at a defined genomic position among a population. A SNP within a coding region, in which both forms lead to the same protein sequence, is termed synonymous; if different proteins are produced they are non-synonymous. SNPs may have consequences for gene splicing, transcription factor binding, or the sequence of non-coding RNA, for example, and/or may indicate the haplotype of the organism.

The term "haplotype" is a contraction of the phrase "haploid genotype", and is presently accepted to mean a set of nucleotide sequence polymorphisms or alleles present on a single maternal or paternal chromosome, usually inherited as a unit.

As used herein, the term "separating" means one or more process used to partially or completely isolate from one another one or more components, and/or one or more process that results in one or more components being no longer located in the same place. The one or more components optionally include, but are not limited to, one or more chromosome types, or single chromosomes, or single copies of a chromosome type. Processes include, but are not limited to, manual, automatic, semi-automatic, remote-controlled, and/or robotic. Illustrative embodiments of such processes include but are not limited to fluorescence activated cell sorting (FACS).

As used herein, the term "hybridization" means one or more processes for co-localizing complementary, single-stranded nucleic acids, and/or co-localizing complementary non-traditional molecules with single- or double-stranded nucleic acids through strand separation (e.g., by denaturation) and re-annealing, for example. In illustrative embodiments, complementary nucleic acid molecules, optionally oligonucleotides, may hybridize to single- or double-stranded DNA. Methods for hybridization are known in the art, and include, but are not limited to, conditions for low and high stringency hybridization (Sambrook and Russell. (2001) Molecular Cloning: A Laboratory Manual 3rd edition. Cold Spring Harbor Laboratory Press; Sambrook, Fritsch, Maniatis. Molecular Cloning: A Laboratory Manual 3.sup.rd edition). Stringency of the hybridization may be controlled (e.g. by the washing conditions) to require up to 100% complementarity between the probe and the target sequence (high stringency), or to allow some mismatches between the probe and the target sequence (low stringency). Factors to determine the appropriate hybridization and wash conditions based on the target and the probe are known in the art. In illustrative embodiments, following the first wash using 0.2× SSC/0.1% SDS for 10 minutes at 68° C., two additional washes with 0.2×SSC/0.1% SDS for 15 minutes each at 68° C. are performed for high stringency washes, two additional washes at 0.2×SSC/0.1% SDS for 15 minutes each at 42° C. for moderate stringency washes, and two additional washes 0.2×SSC/0.1% SDS for 15 minutes each at room temperature for low stringency washes.

The term "allele" as used herein refers to a particular form of a genetic locus, or a genomic region, or an entire chromosome, distinguished from other forms by its particular nucleotide sequence.

The term "locus" as used herein refers to a location on a chromosome or DNA molecule corresponding to a gene or a physical or phenotypic feature.

The term "phased" as used in the context of sequences for two or more polymorphic sites means the sequence present at those polymorphic sites are known whether to be derived from a single chromosome.

The term "unphased" as used in the context of sequences for two or more polymorphic sites on a given chromosome, means the sequences of those polymorphic sites are known individually but it is not known whether they are derived from the same allele of the chromosome. For example, at each polymorphic site, the sequence identities may be known for both copies of the locus of an individual, or multiple copies of a population but it is not known whether they are derived from the same allele of the chromosome.

The term "phased nucleic acid sequence" as used in the context of a single chromosome refers to nucleic acid sequence of a single chromosome where the nucleic acid sequence is obtained from sequencing of a single chromosome. The term "phased nucleic acid sequence" as used in the context of a single chromosomal fragment refers to nucleic acid sequence of a single chromosomal fragment where the nucleic acid sequence is obtained from sequencing of a single chromosomal fragment.

The term "sample" as used herein relates to a material or mixture of materials, typically, although not necessarily, in liquid form, containing one or more analytes of interest.

The term "contacting" means to bring or put together. As such, a first item is contacted with a second item when the two items are brought or put together, e.g., by touching them to each other or combining them in the same solution.

The term "hybridization conditions" as used herein refers to conditions that allow hybridization of a nucleic acid to a complementary nucleic acid. Suitable hybridization conditions may include both hybridization conditions and optional wash conditions, which include temperature, concentration of denaturing reagents, salts, incubation time, etc. Such conditions are known in the art.

The terms "hybridizing", "binding", and grammatical equivalents thereof, with respect to nucleic acids, are used interchangeably.

The phrase "associated with" refers to the situation where a characteristic of a first thing is imparted to a second thing such that the second thing then has that characteristic. For example, a signal associated with a chromosomal fragment refers to a signal that comes from the chromosomal fragment by virtue of oligonucleotides (e.g., labeled oligonucleotides, or oligonucleotides that have molecules which interact to produce the signal, for example, a FRET signal) being hybridized to a region of chromosomal fragment.

The term "chromosomal sample" as used herein relates to a material or mixture of materials, containing chromosomes from a subject.

DETAILED DESCRIPTION

The present disclosure provides methods for determining phased nucleic acid sequence for a single chromosome of interest and/or a single chromosomal fragment of interest. The present disclosure also provides methods for determining phased nucleic acid sequence for a plurality of single chromosomes of interest and/or a plurality of single chromosomal fragments of interest. The plurality of single chromosomes of interest may be of one chromosome type or of two or more chromosome types. The present disclosure also provide a method for isolating a plurality of chromosomal fragments of a specified size range, where the chromosomal fragments are from one or more specified regions of the genome. The plurality of chromosomal fragments may be separated into single chromosomal fragments and sequenced to provide phased nucleic acid sequence for the single chromosomal fragments. Alternatively, the plurality of chromosomal fragments may be sequenced together to provide unphased nucleic acid sequence for the chromosomal fragments.

Methods

As noted above a method for determining phased nucleic acid sequence for a single chromosome of interest is provided. This method may be used to provide phased nucleic acid sequence for a plurality of single chromosomes of interest. The plurality of single chromosomes may be of the same chromosome type or of different chromosome types.

In certain embodiments, this method provides phased nucleic acid sequence for a maternally and a paternally inherited member of a target chromosome pair of a subject. The target chromosome pair may be a pair of any chromosome type of interest. In certain embodiments, a plurality of target chromosome pairs, where the plurality of target chromosome pairs includes pairs of different types of chromosomes may be analyzed using this method.

In general the method includes separating a plurality of chromosomes into individual containers, each container including at most a single chromosome. Amplifying the plurality of chromosomes present in the individual containers to obtain amplified products, where the amplified products produced from the single chromosome present in a first container of the individual containers comprises a first tag and the amplified products produced from the single chromosome present in a second container of the individual containers comprises a second tag, where the first tag is distinguishable from the second tag. The amplified products comprising the first and second tags are mixed together to obtain a mixture of amplified products. The method further includes sequencing the amplified products present in the mixture to obtain sequence information for the amplified products and associating the sequence information to the first or the second tag. The method further includes assigning the sequence information associated with the first tag to the single chromosome present in the first container and assigning the sequence information associated with the second tag to the single chromosome present in the second container. This assigning provides phased nucleic acid sequences for the single chromosomes present in the first and second containers.

In certain embodiments, the method includes separating a plurality of chromosomes of a target chromosome pair into a plurality of single chromosomes present in a plurality of individual containers, where each container includes at most a single chromosome. A target chromosome pair includes a maternally inherited member and a paternally inherited member. A plurality of chromosomes of a target chromosome pair are obtained from a plurality of diploid cells of a subject. A plurality of chromosomes of a target chromosome pair means multiple copies of the maternally and paternally inherited members of the target chromosome pair. A single diploid cell contains two chromosomes of a target chromosome pair, for example.

The method further includes sequencing the plurality of single chromosomes to provide phased nucleic acid sequences for the single chromosomes; grouping the plurality of single chromosomes into two clusters based on the phased nucleic acid sequences, wherein chromosomes within the same cluster have the same sequence at polymorphic sites; and optionally correlating the phased nucleic acid sequences for the single chromosomes to a maternally or a paternally inherited member based on a characteristic known to be associated with a maternally or paternally inherited member. In certain embodiments, the method comprises correlating the phased nucleic acid sequences for the single chromosomes to a maternally or a paternally inherited member based on a characteristic known to be associated with a maternally or paternally inherited member.

In certain embodiments, the sequencing comprises amplifying the plurality of chromosomes to produce amplified products, wherein the amplified products produced from the single chromosome present in a first container of the individual containers comprises a first tag and the amplified products produced from the single chromosome present in a second container of the individual containers comprises a second tag, where the first tag is distinguishable from the second tag; mixing the amplified products produced from the amplifying to provide a mixture of amplified products; sequencing the mixture of amplified products to obtain sequence information for the amplified products and associating the sequence information to the first and second tags. The method further includes assigning the sequence information associated with the first tag to the single chromosome present in the first container and assigning the sequence information associated with the second tag to the single chromosome present in the second container, wherein the assigning provides phased nucleic acid sequences for the single chromosomes present in the first and second containers.

When the two single chromosomes that were sequenced are maternally and paternally inherited members of the target chromosome pair, their sequences will be different at certain polymorphic regions. Thus, the presence of non-identical sequences identifies the two single chromosomes as maternally and paternally inherited members of the target chromosome pair. In certain embodiments, more than two, for example, four or more, six or more, eight or more, ten or more, twelve or more, fifteen or more, seventeen or more, up to, for example, twenty single chromosomes of the same chromosome type may be sequenced in the multiplexed manner described above. Based on the consistency of their sequences at polymorphic sites, the single chromosomes may be clustered (for example, using a statistical clustering method) into two distinct clusters where the chromosomes from the same cluster are of the same parental origin. Accordingly, the phased nucleic acid sequences for the single chromosomes may be correlated to a maternally and a paternally inherited member based on a characteristic known to be associated with a maternally or paternally inherited member.

In certain embodiments, phased nucleic acid sequence for a maternally and a paternally inherited member of a plurality of target chromosome pairs, where the plurality of target chromosome pairs are of different chromosome types may be determined simultaneously using the method described herein. The plurality of target chromosome pairs may be two or more target chromosome pairs, for example, three or more, four or more, five or more, six or more, seven or more, eight or more, nine or more, ten or more, and up to 22 target chromosome pairs for chromosomes obtained from a diploid cell of a male and up to 23 target chromosome pairs for chromosomes obtained from a diploid cell of a female.

In certain embodiments, the chromosomes obtained from diploid cells of a subject may be labeled to provide a labeled population of chromosomes where the chromosomes of interest (target chromosome pair) are distinguishable from the other chromosomes. Methods for labeling and separating different chromosome types are known. For example, different chromosomes may be separated using flow cytometry.

In certain embodiments, the chromosomes may be labeled with one or more DNA labeling dye, such as, Chromomycin (e.g., ChromomycinA3), Hoechst (e.g., Hoechst 33258), propidium iodide, 4,6-diamidino-2-phenylindole (DAPI), mithramycin, and ethidium bromide. In certain cases, bivariate FACS sorting with staining of the chromosomes with Chromomycin and Hoechst may be used to separate the different types of chromosomes. The multiple copies of a type of chromosome may then be separated into single chromosomes.

In certain embodiments, different chromosomes may be identified and isolated using specific fluorescent chromosome paints. For example, chromosome 1 may be labeled with a chromosome 1 specific paint from, for example, Cyto-Cell Technologies (Cambridge, UK), and selectively sorted using FACS. Alternatively, all but chromosome 1, for example, may be painted using chromosome specific paints and FACS used to eliminate the labeled chromosomes. In this manner, chromosome 1, for example, may be isolated in the absence of detecting dye.

The single chromosomes present in individual containers may be amplified using any nucleic acid amplification procedure to provide amplified products, also referred to as polynucleotide products.

Polynucleotide products produced from the amplification of the single chromosomes may be tagged by attaching an oligonucleotide tag to the polynucleotide products. As described above, polynucleotide products produced from amplification of separate single copies of the chromosome (single chromosomes) may be labeled with different tags so that polynucleotide products produced from amplification of a first single chromosome may be distinguished from polynucleotide products produced from amplification of a second single chromosome.

The different tags may be different due to differences in their nucleotide sequences. The differences in the nucleotide sequences of the tag may be determined by sequencing the tags, hybridizing the tag, or any other method known to one of skill in the art.

In one embodiment, all polynucleotide products produced from amplification of a single copy of the chromosome may be tagged with a first tag comprising a first sequence, while all polynucleotide products produced from amplification of another single copy of the chromosome may be tagged with a second tag comprising a second sequence, where the first and second sequences are different.

In another embodiment, all polynucleotide products produced from amplification of a single copy of the chromosome may be tagged with a first tag comprising a first sequence, all polynucleotide products produced from amplification of another single copy of the chromosome may be tagged with a second tag comprising a second sequence, all polynucleotide products produced from amplification of another single copy of the chromosome may be tagged with a third tag comprising a third sequence, where the first, second, and third sequences are different.

By keeping track of which tag was added to amplified products from which single chromosome, the sequence information of the polynucleotide attached to the tag can be traced back to a single chromosome.

Using different tags to track amplification products from single copies of a chromosome may be extended to multiple different chromosomes such that sequences of maternally and paternally inherited chromosomes can be deduced for all of the chromosomes of diploid cells of a subject. By increasing the length of the oligonucleotide tag, one can multiplex hundreds of single chromosome-derived samples, and the amplification and tagging workflow can be automated in a multi-well format, for example, 96-well, 384-well or higher.

A tag may be attached to a polynucleotide amplification product by ligation, polymerase chain reaction, primer extension, and other methods known in the art. In certain embodiments, two or more of these methods may be combined to attach a tag to the polynucleotide amplification products.

In certain embodiments, the entire sequence of a single chromosome may be determined. In other embodiments, only sequence of a region of interest in a single chromosome may be determined. The region of interest may be regions known to or suspected of having polymorphism(s). Thus, the method may be used to provide phased nucleic acid sequence of a single chromosome of interest.

In certain embodiments, a plurality of single copies of a chromosome (i.e., single chromosomes) is sequenced to reconstruct the phased sequences of the target chromosome. As noted above, the entire chromosome may be sequenced (for example, 70% or more, or 75% or more, or 80% or more, or 85% or more, or 90% or more, or 95% or more, or 99% or more, of the chromosome) to provide a completely phased sequence of the target chromosome. In certain cases, two or more single copies, or three or more single copies, or four or more single copies, or five or more single copies, or six or more single copies, or seven or more single copies, or eight or more single copies, or more of the target chromosome may be sequenced as described above.

Any method for sequencing a nucleic acid may be utilized. Methods for sequencing nucleic acid fragments are well known and are described in, for example, US Pub No. 20100105052; Murphy, K.; Berg, K.; Eshleman, J. (2005) Clinical chemistry 51 (1): 35-39; Stein R A (1 Sep. 2008) Genetic Engineering & Biotechnology News 28 (15), which are hereby incorporated by reference. In certain embodiments, high-throughput sequencing may be utilized by using commercially available sequencing platforms, such as those available from Lynx Therapeutics, 454 Life Sciences, Illumina, Pacific Biosciences, Applied Biosystems, and the like.

The sequences obtained from sequencing of the amplification products obtained from a single chromosome of a target chromosome pair may be analyzed using a computer. A computer used to analyze the sequence information may be a specific computer programmed to run a software, e.g., a program for analyzing the sequence information.

The phased nucleic acid sequences for the single chromosomes may be correlated to a maternally and/or a paternally inherited member of the target chromosome pair, via direct deduction from cross referenced paternal or maternal nucleic acid sequence (obtained from family studies), if either is available. The paternal or maternal nucleic acid sequence need not be phased, although phased sequence has more discerning power in certain cases. If neither paternal nor maternal nucleic acid sequence is available, nucleic acid sequences from other close relatives are useful in such deductions.

The phased nucleic acid sequences for the single chromosomes may be correlated to a maternally and/or a paternally inherited member based on a characteristic known to be associated with a maternally or paternally inherited member. In certain cases, a characteristic known to be associated with a maternally or paternally inherited member of the target chromosome pair is imprinting where a gene present in the target chromosome pair is known to be maternally or paternally methylated. In other words, a maternally imprinted gene means that if the chromosome is maternally inherited then the gene is methylated, whereas if the chromosome is paternally inherited then the gene is unmethylated. In certain cases, the method includes extracting methylated chromosome, for example, by using immuno-precipitation with an antibody for methylated chromosome. The methylated chromosome may then be sequenced as explained above to provide a phased nucleic acid sequence for the single methylated chromosome (or a plurality of single methylated chromosomes separated into individual containers). As such, the sequence reads that map to a maternally (or paternally) imprinted locus would come from only the maternally (or paternally) inherited chromosome.

In certain cases, a characteristic known to be associated with a maternally or paternally inherited member of the target chromosome pair is the maternal (or parental) allele specific expression of certain genes. For example, a paternally expressed gene is one that is expressed when the chromosome was inherited from the father but not expressed when the chromosome was inherited from the mother. For example, if sequences from the mRNA of the paternally expressed gene are obtained, then the sequence reads would be derived from the version of the gene that was inherited from the father.

To assign the two phased chromosome sequences to the maternally and the paternally inherited chromosomes, a parentally or maternally imprinted gene on that chromosome may be selected, for example, for Chr1 PEG10 (paternally expressed gene 10) may be used. The genomic region and the transcript of PEG1 are about 27,000 and 2,000 bp long, respectively. Since on average polymorphic sites occur once every 200-300 bp, at least one heterozygous sites would be present in this region. The heterozygous site(s) within this region may be analyzed to obtain allele-specific transcription or allele-specific methylation measurements to determine which allele of chromosome 1 is maternally transmitted (namely the one carrying the imprinted version of PEG10). In certain embodiments, another imprinted genes on the chromosome can be used instead of or in combination with PEG10.

Genomic imprinting is a parental origin-specific gene silencing that leads to differential expression of the two alleles of a gene in mammalian cells. In certain cases, a gene present in the target chromosome pair may be maternally or paternally methylated. For a maternally imprinted gene, if a chromosome of a target chromosome pair is maternally inherited then the gene is methylated, whereas if the chromosome is paternally inherited then the gene is unmethylated. Numerous approaches may be used to identify CpG islands that are differentially methylated in a chromosome type. These approaches are described in Toyota, M., et al., (1999) Cancer Res. 59, 2307-2312; Huang, T. H.-M., et al., (1999) Hum. Mol. Genet. 8, 459-470; Shiraishi, Chuu, Y. H., & Sekiya, T. (1999) Proc. Natl. Acad. Sci. USA 96, 2913-2918; Hayashizaki, Y., et al. (1994) Nat. Genet. 6, 33-40; Plass, C., et al. (1996) Nat. Genet. 14, 106-109; Brock, G. J. R., Charlton, J., & Bird, A. P. (1999) Gene 240, 269-277; United States Patent Application Publication No. 20100273658, which are herein incorporated by reference. Alternatively or in addition, standard methods for sequencing mRNA can be used to obtain the mRNA sequence of the imprinted gene, for example, one can use PCR to amplify the transcripts of the gene and then sequence the amplified products.

The method described herein may be used for determining the parental origin of each of the 46 chromosomes of an individual without the need of any data from his or her relatives. This means that for each chromosome type except ChrY, i.e., for Chr1, Chr2, and up to Chr22, and also for ChrX if the individual is female, the sequence of the maternally transmitted chromosome and also that of the paternally transmitted chromosome may be determined. Once the two parentally transmitted sequences of each of the chromosome types (i.e. the two phased sequences for each chromosome type) has been obtained as described herein, the two phased chromosome sequences are assigned to the maternally and the paternally inherited chromosomes, as described above.

Any diploid cell of a subject may be used in the above methods. In certain cases, the diploid cell may be obtained from blood, tissue, organ, solid tumor, etc. of a subject. In certain embodiments, the diploid cell from which chromosomes are isolated include buccal cells, lymphocytes, skin cells, etc.

The diploid cells may be lysed by a number of techniques that do not adversely affect the integrity of the chromosomes present in the cells. The technique may be a physical or chemical disruption of the cells or a combination thereof. For example, hypotonic lysis and/or proteinase K lysis may be used.

Also provided herein is a method for the generation of distance information on sequence reads based on the use of flow cytometry to isolate single copies of large DNA fragments. In certain embodiments, the method includes fragmenting a collection of chromosomes which are: (i) of a specific chromosome type (e.g., obtained through chromosome sorting) or (ii) a mixture of different chromosome types. In certain cases, the fragmenting produces large chromosome fragments of a targeted size range (e.g., from 10 kb to the full length of the chromosome, 1-50 megabases, for example, 1-40 megabases, 1-30 megabases, 1-20 megabases, 1-10 megabases, or 1-5 megabases). The large chromosome fragments may be about 1 megabase in length, or about 3 megabase in length, or about 10 megabase in length, or about 15 megabase in length, or about 20 megabase in length, or about 25 megabase in length, or about 30 megabase in length, or about 40 megabase in length, or about 50 megabase in length. The fragmenting may be carried out by physical or enzymatic means. The large chromosome fragments may then be separated into single fragments. The single chromosome fragments may then be sequenced and the sequence analyzed as described herein. All the reads generated from a single fragment would be collocated within a genomic region within the targeted size range (e.g. from 10 kb to the full length of the chromosome, 1-50 megabases). Therefore, this method generates distance information among the resulting sequence reads. Furthermore, when the fragments are separated into single fragments by using a FACS instrument, the FACS instrument can provide approximate size estimate of the sorted fragment and thus the size of the fragment that was sequenced is approximately known.

This distance information is invaluable for solving a major problem in the use of next generation sequencing methods to obtain novel genome sequences. In the de novo determination of genome sequences, billions of short reads need to be assembled into a small number of linear sequences corresponding to the different chromosomes types. This is a much harder problem than re-sequencing which relies on alignment of the reads to a reference genome. In fact, de novo assembly of the large genomes (such as those in higher eukaryotes) is probably infeasible if based only on short reads (i.e., hundreds of by in size) sampled from the genome. It is long known that some type of distance information between pairs or groups of reads will be essential for this assembly task. In the early days of the human genome project, this distance information was provided by physically cloning a large chromosome fragment (say 1 megabase in size) as a yeast artificial chromosome (YAC). Knowing that a group of reads is derived from the same YAC then allows the assembling of this group of reads into a sequence "contig" without having to worry about aligning them to all the other reads in the sequencing project. The method described herein replaces the laborious step of cloning into YACs or BACs (bacterial artificial chromosomes) by the use of single fragments. Moreover, the reads with distance information provided by the above method can be used to supplement the reads obtained by any standard short-gun sequencing protocol so as to make the assembly of all the reads feasible.

As a by-product, this method would also provide phasing information as long as the two polymorphic sites can be covered by a fragment within the targeted size range.

Also provided herein are methods for isolating specific genomic regions of interest based on the use of flow cytometry. This method may be used to efficiently isolate chromosomal fragments containing matches to a set of targeting nucleic acid sequences which are specific short sequences designed to identify a genomic region of interest. The set of targeting sequences may include one or more pair of short sequences, with the property that each pair of short sequences produce a detectable signal when present in close proximity to one another. Thus, when both members of a pair of short sequences are annealed to a complementary region in the target genome, a signal is produced. The chromosomes containing the target region of interest may be fragmented to obtain chromosomal fragments. The chromosomal fragments hybridized to the set of targeting nucleic acid sequences. When a chromosomal fragment includes the genomic region of interest, both members of a pair of short nucleic acid sequences bind to it and produce a detectable signal. Based on the presence of the signal, the chromosomal fragment may be isolated and sequenced to provide a sequence of the genomic region interest. Accordingly, the sequence of the genomic region interest may be assembled by sequencing overlapping chromosomal fragments obtained by the above method.

In certain embodiments, a first member and a second member of a pair of short nucleic acid sequences (also referred to as oligonucleotides) include a donor and an acceptor molecule, respectively. The presence of the first and second members of a pair of short nucleic acid sequences in vicinity of each other produces a fluorescence resonance transfer (FRET) interaction providing a detectable signal which is used to separate the chromosomal fragment to which the pair of oligonucleotides is bound. Donor and acceptor molecule pairs known to produce a FRET signal are well known.

The specific short sequences may range from 25 bases to 250 bases in length, for example, 30 bases to 230 bases, 40 bases to 200 bases, 50 bases to 150 bases, 80-100 bases, for example, 100 bases in length.

Utility

The key role of genetic variants in regulating allele-specific gene expression and alternative splicing was recently demonstrated through RNA sequencing (Pickrell J K, et al. (2010) Nature 464(7289):768-772; Montgomery S B, et al. (2010) Nature 464(7289):773-777). These analyses can be enhanced and extended by using the completely phased SNP information uncovered from the methods described above.

The present methods provide a reliable method for providing information of heterozygous SNPs, especially when compared to the traditional (unphased) genome sequencing. The heterozygous SNP calling procedure described herein (see examples below) requires not only a bimodal distribution of reads over the nucleotide identities (i.e. two different nucleotides each appearing multiple times), but also that the reads containing the same nucleotides must have tags associated with the same parental allele (chromosome derived from a parent). This is a powerful restriction that makes variant calling much stronger at heterozygous bases in the person's diploid genome.

Long-range phase information derived using the methods described herein may be used for studies of human diseases. For example, the association of haplotypes as large as 12 Mb was found to be significant for transplant rejection (Chen Y, Cicciarelli J, Pravica V, & Hutchinson I V (2009) Mol Immunol 47(1):96-100); admixture mapping (Winkler C A, Nelson G W, & Smith M W (2010) Annu Rev Genomics Hum Genet. 11:65-89) of disease loci may be made more powerful if phasing can be directly determined as disclosed here rather than inferred via complex statistical models.

Phased nucleic acid sequence or long-range haplotype information obtained by the methods described herein is important in understanding distal cis-regulation of spatially and temporally specific gene expression in development (Kleinjan D A & van Heyningen V (2005) Am J Hum Genet. 76(1):8-32). Phased nucleic acid sequence or long-range haplotypes determined using the methods described herein may be useful in studies of human adaptation by determining which are signals of recent positive selection (Sabeti P C, et al. (2002) Nature 419(6909):832-837. Pritchard J K, Pickrell J K, & Coop G (2010) Curr Biol 20(4):R208-215). Phased nucleic acid sequence or long-range haplotypes determined using the methods described herein may be useful in determination of recombinant haplotypes which provide insight into population history (Nunome M, et al. (2010) Mol Ecol 19(12):2474-2489).

Phase-Seq method as described herein provides a foundation for resolving the role of parental origin specific genetic variants in disease association, allele-specific gene expression and alternative splicing (Kong A, et al. (2009) Nature 462(7275):868-874, Pickrell J K, et al. (2010) Nature 464(7289):768-772, Montgomery S B, et al. (2010) Nature 464(7289):773-777).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods

Blood sample and chromosome preparation. Human blood samples for chromosome sorting were donated by an anonymous donor. Each sample is tested free of viral infection prior to experiment. Chromosomes were prepared by using a slight modification of a described method (Fantes J A & Green D K (1990) Methods Mol Biol 5: 529-542). Approximately 8 ml of residual leukocytes obtained from LRS chamber pheresis were first enriched with RosetteSep DM-L (StemCell Technologies, British Columbia, Canada). The lymphocytes were washed twice with PBS+2% fetal calf serum and were counted before cultured at $0.5 \times 10^6$ cells/ml in RPMI complete medium containing 10% fetal calf serum and 10 μg/ml Phytohemagglutinin-M (Roche, Germany). After 50 hour (h) incubation (37° C., 5% $CO_2$), Demecolcine (Sigma, Mo.) was added to the medium at 0.1 μg/ml and the cultures were harvested 14 h later.

To prepare chromosomes for sorting, the cells were first swelled in freshly-made hypotonic solution at room temperature for 10 min. Then, the cells were spun down and the pellet was resuspended in ice-cold polyamine buffer for 15 min. To break the cell walls, the cells were vortexed vigorously for 30-60s at 4° C., and the cell suspension was transferred into 1.5 ml eppendorf tubes. Subsequently, the nuclei were removed from the chromosome suspension by centrifugation at 100×g for 3 min. 750 μl of chromosome suspension was placed into 12×75 mm tubes for the flow cytometer. To stain the chromosomes, 20 μl Chromomycin A3, 2 μl Hoechst 33258 stain and 20 μl 100 mM magnesium sulphate were added to each tube.

Influx setup for chromosome sorting. Chromosome sorting was performed on a BD InFlux cell sorter. A 70 t nozzle was used with a sheath pressure of 40 psi. Excitation of Hoechst and Chromomycin was done with solid state 100 mW 355 nm laser and a 200 mW 457 nm laser, respectively. Emission of the Hoechst fluorescence was collected with a 460/50 bandpass filter, and the Chromomycin fluorescence with a 550/50 bandpass filter. The UV laser was timed as the first laser and detection was triggered by Hoeschst fluorescence. For Phase-Seq analysis, individual sorted chromosome was collected in a well of a low-profile 96-well unskirted PCR plate (Bio-rad, CA), and the plate was sealed and stored at −80° C. freezer before experiment. The steam control is collected in 1.5 ml DNase/RNase-free eppendorf tubes.

Single chromosome amplification. Twenty-eight single Chr19s, along with twelve controls (negative controls: no target, FACS stream; positive control: human total DNA), were separately amplified using the Picoplex WGA Kit (Rubicon Genomics) according to the manufacturer's protocol (version R30050-09). Amplified DNA was then column purified. Using sequence specific PCR primers, Chr19 specific DNA sequences were verified on the amplified single chromosome samples (except the low yield ones) and positive controls, but not on the negative controls (data not shown).

Multiplex Illumina GAIIx Sequencing. The adapter pair used in Illumina GAIIx sequencing were synthesized by Elim Biopharmaceuticals, Inc. The adapter pair set consists of two designs. Design PETP (5'-PE-Tag-Picoplex-3'), in which the standard Illumina PE1/PE2 adapter pair:

```
                                     (SEQ ID NO: 03)
5'-ACACTCTTTCCCTACACGACGCTCTTCCGATCT-3'
and
                                     (SEQ ID NO: 04)
5'-CTCGGCATTCCTGCTGAACCGCTCTTCCGATCT-3',
``` each adjoined in tandem with a 6-base multiplex tag and a 18-base Picoplex linker sequence, were introduced via PCR onto the ends of amplified single chromosome DNAs. This Picoplex linker served as a linker to adjoin the Illumina PE adapter/multiplex tag pair to the Picoplex amplified DNA, as in the case of standard Illumina PE adapters. A subset of experiments used an alternative adapter pair set design, adapter pair set PENTP (5'-PE-Nonamer-Tag-Picoplex-3'), which introduced a stretch of 9 random nucleotides (random nonamer) placed between the Illumina PE adapter sequence and the 6-base multiples tag.

Illumina PE sequencing libraries were then generated according to Illumina's standard protocol, except that, to preserve the single chromosome amplified DNA, the libraries consist a size distribution of 200-1000 bases, rather than size-selected to a narrower range. Unincorporated adapters and adapter dimmers were removed from the libraries using the Agencourt AMPure XP system (Beckman Coulter). The 6-base multiplex tag allowed 12 sequencing libraries to be combined into one pool and loaded onto a single lane on the Illumina GAIIx system for single read 101-base or 108-base runs (Ohio State University Nucleic Acid Shared Resource Facility).

Sequence data analysis. The image data from Illumina GAIIx sequencing were analyzed using the next_phred software package. Briefly, image data were processed through a initial base-calling process, aligned to the February 2009 human whole genome reference sequence (GRCh37); the base calling were then calibrated and cluster reads were obtained. Based on next_phred's base calling quality score and excluding the adapter sequence, the reads were end trimmed and aligned to the human whole genome reference sequence, allowing a next_phred mapping quality score cutoff of 100 or 60 (see below) and individual base next_phred quality score cutoff of 15. An initial sequencing data analysis using the default Illumina Pipeline 1.6 software generated suboptimal results which were not used in subsequent analysis.

Complete phasing by clustering of single chromosomes into parental allele groups. Because amplified DNA from each single chromosome is absolutely in phase with each other, there are only two types of haploid chromosomes (i.e. two parental alleles for Chr19) among the 28 single Chr19 derived samples. Of the 28 Chr19s, 9 of them gave rise to very low numbers of tagged reads. These tags were removed from all subsequent analyzes. The tag association for the sequencing reads with the remaining tags were determined, keeping only reads with a next_phred read quality score average of 15 or higher on the 6-base tags. To cluster the tags into two groups corresponding to the two parental alleles, first, for each pair of tags, it was analyzed whether their reads at polymorphic sites are consistent with each other. For a given pair of tags, examined a set of SNP sites on Chr19 were and a consistency index for the tag-pair was obtained by computing the percentage among this set of sites at which there was identical majority vote from the tags. The majority vote from a tag at a SNP site is defined as the nucleotide (G, C, A or T) with the highest read count from that tag. It is important that a reliable and unbiased set of SNP sites are used in the above computation of the pairwise consistency indexes. To obtain this set of SNPs, we applied the de novo SNP calling program phastlane of the next_phred package to analyze the aligned reads. In total, phastlane output 12326 putative SNPs of which 7709 are putative heterozygous SNPs with 2 or more base identities, and 4617 are putative homozygous SNPs with only 1 base identity, which is different from the reference sequence. Since the phastlane computation did not make use of the tag information, it did not induce any bias on the consistency indexes between pairs of tags. Therefore, if the two single chromosomes associated with the two tags are copies of the same parental allele of Chr19, then the pairwise consistency index should be very close to 1. On the other hand, if the two single chromosomes are copies of different parental alleles, then their consistency index should be much lower than 1, as the consistency should be close to zero on heterozygous SNPs. Filtering criteria for these putative SNPs was applied, using an individual base quality score of 15 or higher, and a next_phred mapping quality score of 100 or higher for the associated read. To further increase the reliability of clustering, in the actual computation of the pairwise consistency index, any phastlane detected SNP positions that has less than 3 reads from either one of the tags were removed, before the percentage of positions where the two tags agree on their majority vote was computed. Table 1 presents the pairwise consistency indexes for the 19 tags. Based on the table, it was concluded with high confidence that tags 1, 3, 7, 8, 9, 10, 11, 14, 23, 24 belong to one of the parental allele, and tags 2, 4, 5, 6, 12, 15, 16, 19, 22 belong to the other parental allele.

Scanning of heterozygous and homozygous SNPs. Making use of the tag to parental allele association, the whole Chr19 was scanned to obtain SNP positions. First, low quality reads were filtered out using the following criteria: next_phred mapping quality score of 60 or higher for the aligned read, individual base quality score of 15 or higher for the putative SNP. For each position in Chr19, define n1 as the number of reads from allele 1 that support the most frequent base at this position, and m1 as the number of reads that support the next most frequent base. Similarly, define n2, m2 from allele 2. The position is called a heterozygous SNP position if i) the most frequent base in allele 1 is different from that in allele 2, ii) $n1 \geq 4$, $n1-m1 \geq 2$, $n1/m1 \geq 1.5$, and iii) $n2 \geq 4$, $n2-m2 \geq 2$, $n2/m2 \geq 1.5$. It is called a homozygous SNP position if condition (i) is replaced by the condition that the most frequent base in allele 1 is identical to that in allele 2, but different from that in the reference genome. This is a stringent calling procedure that requires at least 4 reads from each allele, as well as additional conditions on the distribution of reads within the same allele. By this method, a total of 6444 heterozygous SNPs and 3694 homozygous SNPs were identified. To increase SNP detection sensitivity, we used all the reads with next_phred alignment score $\geq 60$ (instead of 100) in the above scan. As the consensus calls may not be as reliable as ones achieved based on reads with alignment score $\geq 100$ as in the computation of pairwise consistency, assessment of the reliability of a consensus call for each allele at each detected SNP position was performed by computing its consensus score, which is defined as the ratio of the number of reads supporting the consensus call to the total number of reads at that position from that allele. The distribution of the consensus scores from both alleles and all heterozygous SNPs was graphed. The distribution appeared to be bi-modal with a dividing value around 0.8. The calls with low consensus scores may be contaminated by poorly aligned reads. Any SNP positions where one or both consensus calls have low consensus score values (<0.8) was removed. 5281 out of 6444 heterozygous SNPs, and 3159 out of 3694 homozygous SNPs remain after this filtering step. To calculate the Ti/Tv ratio, all SNPs from either parental allele which make the consensus score cutoff were compared against the reference genome. These SNPs spanning Chr19 was obtained with a moderate coverage of Chr19 (~8x).

Detection of indels. Sequencing reads were aligned to the reference sequence (GRCh37) using the phaster program of the next_phred package as described in the previous sections, except that indels of up to 3 nucleotides are set to be allowed via the program parameters. Positions where the indels occur were identified, and SNP scanning of these positions were conducted similarly as in the whole genome SNP scan described previously, except that, to compensate the more leniency in alignments allowing indels, more stringent criteria are used in conditions ii) $n1 \geq 5$, $n1-m1 \geq 3$, $n1/m1 \geq 1.5$, and iii) $n2 \geq 5$, $n2-m2 \geq 3$, $n2/m2 \geq 1.5$.

Example 1

Phase-Seq Method

Chromosome sorting was used to isolate single copies of a chromosome. Each copy was separately amplified and the products were tagged by a short stretch of nucleotides before being pooled together (multiplexed) for massively parallel sequencing (FIG. 1). The tag allowed assignment of a read back to the single chromosome copy that gave rise to it. Statistical analysis was performed based on the status of polymorphic sites, to cluster the single copies of the chromosome into two clusters, so that the copies in the same cluster are from the same parental allele. In this way after sampling a sufficient number of reads from each allele, the paternal and maternal haploid genome sequences were separately reconstructed. This method is termed Phase-Seq. The steps of this method are described in detail below.

Blood samples of a donor individual and collected single chromosomes using FACS mediated single chromosome sorting (Carrano A V, Gray J W, Langlois R G, Burkhart-Schultz K J, & Van Dilla M A (1979) Proc Natl Acad Sci USA 76(3):1382-1384), which identifies each chromosome by its distinct bivariate distribution of fluorescent signals from the staining of Chromomycin A3 (binds GC-rich regions) and Hoechst 33258 (binds AT-rich regions) staining. 28 single copies of chromosome 19 (Chr19) were collected and amplified separately, along with 12 control samples. Chr19 specific DNA sequences were verified on the single chromosome samples and positive controls, but not on the negative controls, using sequence specific PCR primers. The 28 single chromosome samples were then sequenced in a multiplex sample format which included 12 samples per lane on an Illumina GAIIx sequencer, with each sample uniquely identifiable by a 6-base index tag. Five lanes of sequence image data were obtained and analyzed using the next_phred software by Phil Green. FIG. 1 illustrates the workflow.

FIG. 1 provides a schematic diagram of the haploid genome resolution work flow. Single chromosomes were sorted into wells of a 96-well plate, in which single chromosome amplification were performed. Each amplified DNA molecule from a single chromosome (e.g., Chr19) contain a specific tag (shown in red or blue) that allow multiplex sequencing on a high throughput sequencing platform. Multiplexed reads were assigned to haploid genomes based on the combination of single chromosome specific tag (shown in red or blue), and haploid genome specific SNPs (in small case of italic bold type). Insert: FACS sorting of stained single chromosomes are based on the fluorescence patterns of Hoechst and the Chromomycin which allow reliable separation of different chromosomes (Chr18 and Chr19 are shown).

Figure 2A:
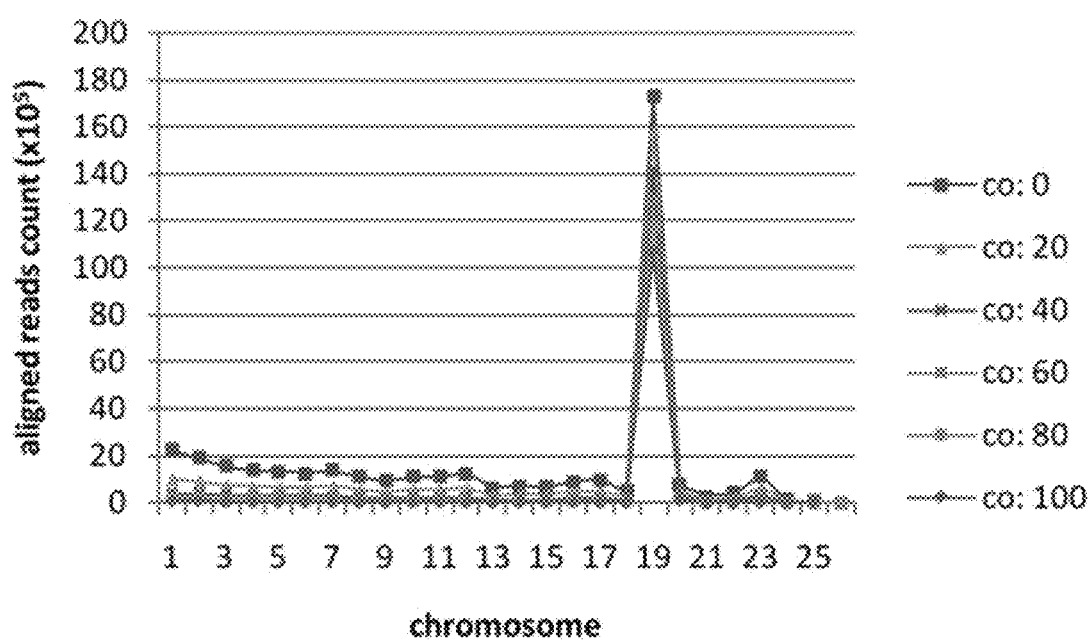
FIGS. 2A-2C illustrate that sequence reads from sorted and amplified single chromosomes predominantly map to Chr19.
Figure 2B:
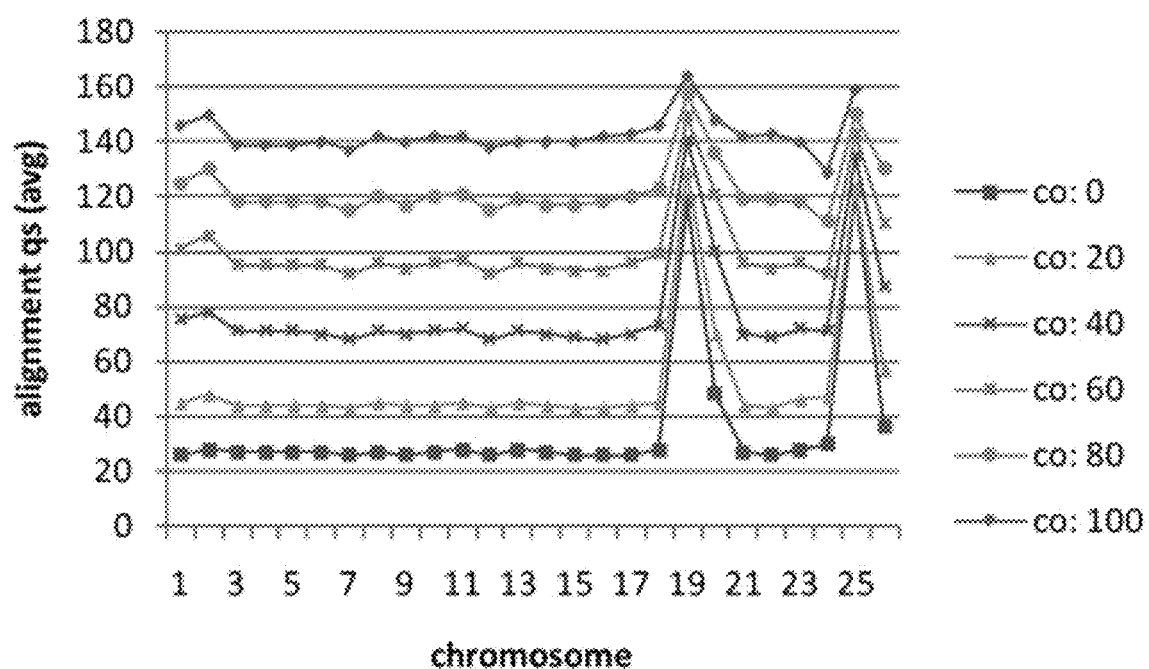
Figure 2C:
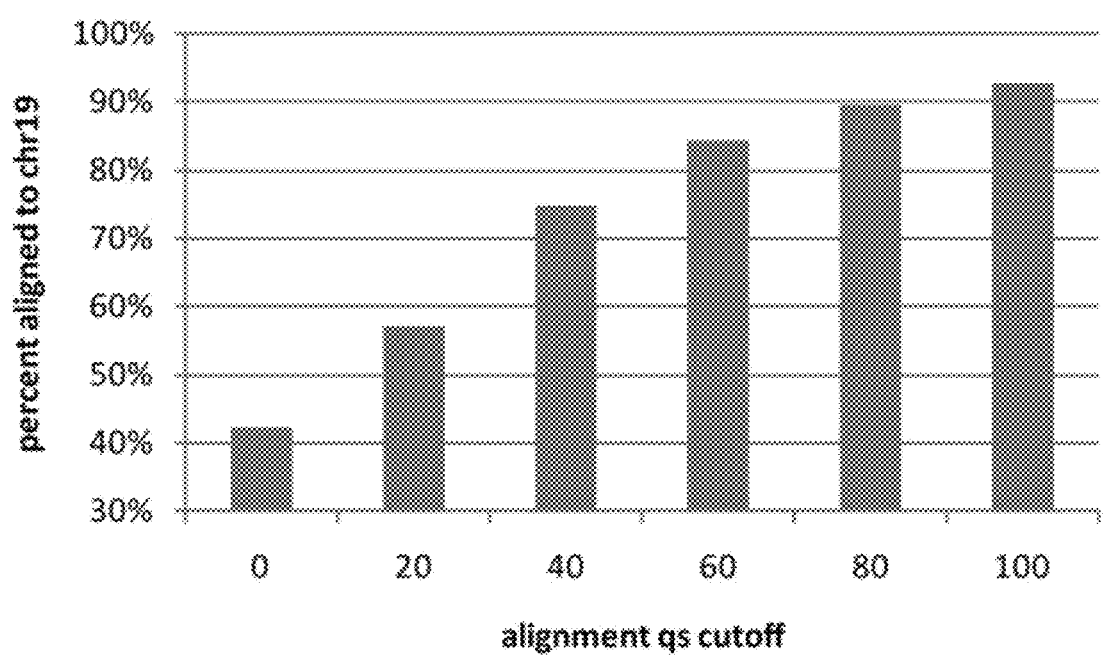

FIG. 2 shows that the reads predominantly map to Chr19 (FIG. 2A). Alignments to other chromosomes generally have much lower mapping quality scores (FIG. 2B). The percentage of the reads mapped to Chr19 increases from 40% to 93% when the mapping quality score cutoff is increased from 0 to 100 (FIG. 2C). These results indicate that copies of Chr19 were obtained with high specificity, and that the amplification and sequencing procedures preserved this specificity.

To analyze the distribution of the reads, Chr19 was divided into non-overlapping windows of 100 Kb size. For each window the percentage of positions within the window that are covered by reads was computed. The result (FIG. 3A) showed that generally about 40% of the positions were covered, and 20% were covered by 5 or more reads. Exceptions to this are the centromere region which has no reads and a 4.5 Mb region which has lower than average counts. Excluding the centromere region, the largest gap is 63 Kb in size, and only 40 gaps are larger than 5 Kb (FIG. 3B). The sum of all gaps of size larger than 1 Kb is 4579 Kb which is still a small fraction of Chr19. Thus the amplification from single chromosomes had yielded a relatively unbiased coverage of the whole chromosome.

Figure 3A:
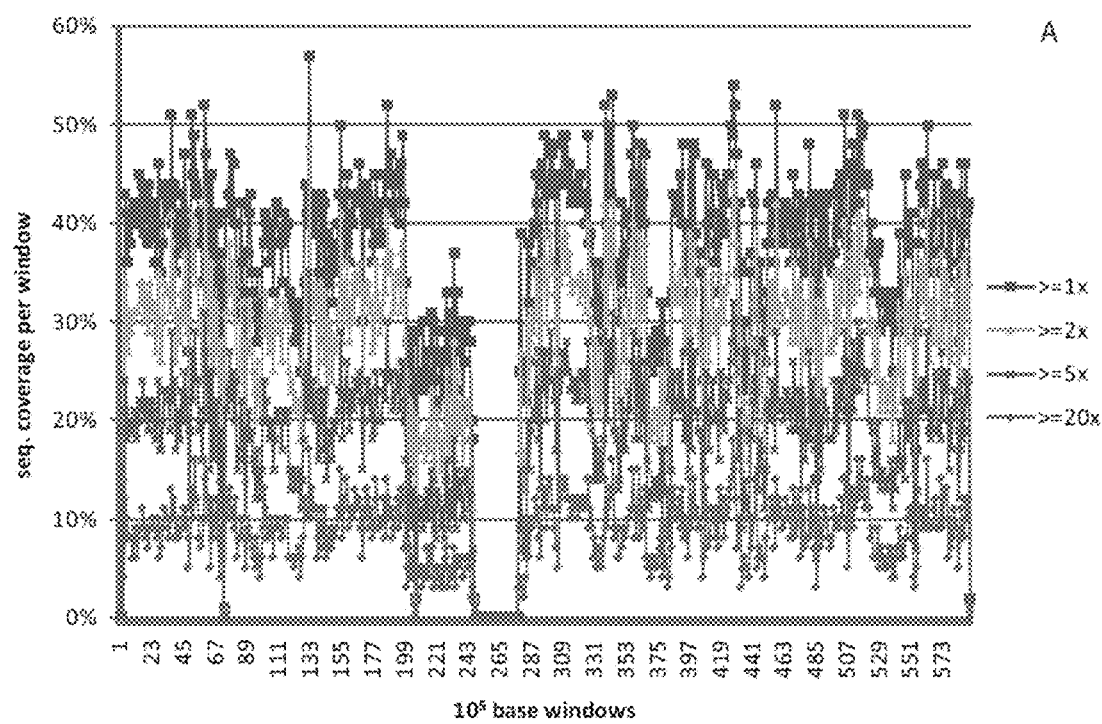
FIGS. 3A-B illustrate the distribution of reads along Chr 19.
Figure 3B:
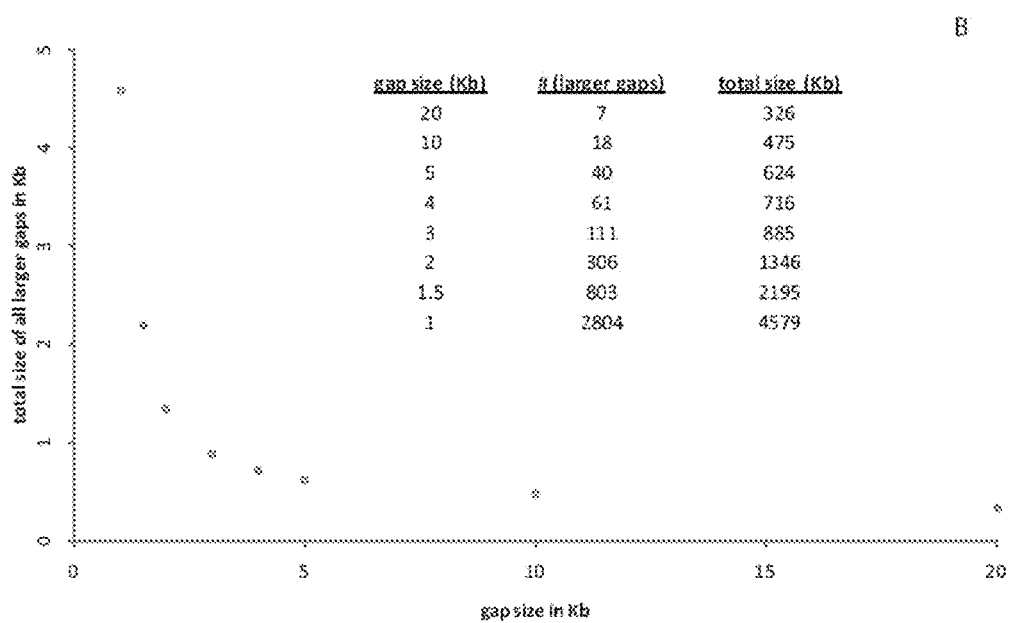

FIG. 3 shows distribution of reads along Chr19. (FIG. 3A) The full span of Chr19 is divided into about 600 non-overlapping windows of size 105 base each, and the counts of high-quality reads (next_phred mapping quality $\geq 100$) for each window are displayed as color coded data points, indicating the percentage of bases in each window being covered by the reads for at least once (red), twice (green), five (purple) and twenty (blue) times. (FIG. 3B) Plot of total size of all gaps exceeding a certain size threshold. Details are given in insert table, e.g., there are 18 gaps larger than 10 Kb and in total they covered 475 Kb of Chr19.

The reads were then assigned to individual single chromosomes according to the unique tag sequence for each sample. Nine of the 28 tags have very low read counts, indicating failure of amplification. These were removed from all subsequent analysis. For the remaining 19 tags, it was attempted to associate each of them with one of the two parental alleles. Using the de novo SNP calling program phastlane of the next_phred package to analyze each lane separately without using the tag information, 12326 putative SNP positions were obtained that are either heterozygous or homozygous (i.e., identical in the two haploid genomes, but different from the corresponding base in the reference genome sequence). Base identities at these positions from sequencing reads were analyzed, and the pairwise consistency between pairs of tags of reads containing these SNPs were obtained. As shown in Table 1, single chromosomes can be cleanly divided into two clusters (see methods for the computation of consistency indexes and clustering).

For a given pair of tags, consider all SNP positions detected by next_phred that are supported by 3 or more reads of mapping score≥100, from each tag in the pair. The pairwise consistency index is defined as the percentage of such SNP positions where the same nucleotide (C, G, A or T) is found to have the highest frequency in each of the two tags. The bottom row displays the accumulated count for a tag used in the pairwise comparison.

Cluster 1 has 10 single chromosomes corresponding to tags 1, 3, 7, 8, 9, 10, 11, 14, 23, 24; and cluster 2 has 9 single chromosomes corresponding to tags 2, 4, 5, 6, 12, 15, 16, 19, 22. The within-cluster agreement is excellent (average consistency=97.5%). The between-cluster consistency is much lower (around 50%) but not close to zero because there must be agreement between tags on the homozygous SNP positions. It was concluded that the single chromosomes within a cluster can be regarded as copies from the same parental allele of Chr19. In total, 176676 reads were assigned to allele 1 (of chr19), and 162049 reads were assigned to allele 2.

Making use of the read to parental allele association, Chr19 was scanned for heterozygous SNP positions where there is a consensus call for each allele but the two consensus calls disagree with each other, and also for homozygous SNP positions where the consensus calls for the two alleles are identical to each other but different from the reference sequence. In

TABLE 1

Consistency indexes between pairs of tags.

|        | 1    | 3    | 7    | 8    | 9    | 10   | 11   | 14   | 23   | 24   |
|--------|------|------|------|------|------|------|------|------|------|------|
| 1      |      | 96%  | 94%  | 95%  | 95%  | 95%  | 95%  | 94%  | 96%  | 96%  |
| 3      | 96%  |      | 95%  | 97%  | 96%  | 96%  | 95%  | 100% | 98%  | 97%  |
| 7      | 94%  | 95%  |      | 95%  | 97%  | 96%  | 97%  | 98%  | 85%  | 97%  |
| 8      | 95%  | 97%  | 95%  |      | 97%  | 93%  | 98%  | 100% | 98%  | 97%  |
| 9      | 95%  | 95%  | 97%  | 97%  |      | 98%  | 95%  | 100% | 98%  | 99%  |
| 10     | 95%  | 96%  | 96%  | 93%  | 99%  |      | 91%  | 100% | 98%  | 96%  |
| 11     | 95%  | 95%  | 97%  | 96%  | 95%  | 91%  |      | 98%  | 97%  | 97%  |
| 14     | 94%  | 100% | 98%  | 100% | 100% | 100% | 98%  |      | 100% | 100% |
| 23     | 96%  | 95%  | 95%  | 93%  | 98%  | 98%  | 97%  | 100% |      | 97%  |
| 24     | 96%  | 97%  | 97%  | 97%  | 99%  | 96%  | 97%  | 100% | 97%  |      |
| 2      | 28%  | 25%  | 25%  | 26%  | 26%  | 38%  | 24%  | 25%  | 27%  | 25%  |
| 4      | 26%  | 53%  | 45%  | 46%  | 44%  | 44%  | 45%  | 24%  | 46%  | 44%  |
| 5      | 23%  | 44%  | 43%  | 46%  | 47%  | 46%  | 42%  | 40%  | 44%  | 49%  |
| 6      | 26%  | 50%  | 45%  | 46%  | 44%  | 45%  | 45%  | 32%  | 47%  | 23%  |
| 12     | 25%  | 52%  | 52%  | 52%  | 54%  | 48%  | 49%  | 30%  | 47%  | 44%  |
| 15     | 24%  | 49%  | 31%  | 53%  | 53%  | 47%  | 49%  | 31%  | 61%  | 57%  |
| 16     | 25%  | 43%  | 52%  | 55%  | 56%  | 47%  | 42%  | 36%  | 51%  | 52%  |
| 19     | 22%  | 47%  | 50%  | 50%  | 51%  | 42%  | 47%  | 36%  | 48%  | 55%  |
| 22     | 22%  | 49%  | 55%  | 50%  | 53%  | 49%  | 47%  | 31%  | 56%  | 55%  |
| counts | 3460 | 3196 | 3994 | 4815 | 3249 | 3852 | 4565 | 624  | 2705 | 2833 |

|        | 2    | 4    | 5    | 6    | 12   | 15   | 16   | 19   | 22   |
|--------|------|------|------|------|------|------|------|------|------|
| 1      | 28%  | 28%  | 23%  | 26%  | 25%  | 24%  | 25%  | 22%  | 22%  |
| 3      | 26%  | 53%  | 44%  | 50%  | 52%  | 49%  | 49%  | 47%  | 49%  |
| 7      | 25%  | 45%  | 43%  | 45%  | 52%  | 51%  | 52%  | 50%  | 55%  |
| 8      | 25%  | 46%  | 46%  | 46%  | 52%  | 53%  | 55%  | 50%  | 50%  |
| 9      | 28%  | 42%  | 47%  | 44%  | 54%  | 53%  | 56%  | 81%  | 55%  |
| 10     | 25%  | 44%  | 46%  | 45%  | 48%  | 47%  | 47%  | 42%  | 49%  |
| 11     | 24%  | 45%  | 42%  | 43%  | 49%  | 49%  | 48%  | 47%  | 47%  |
| 14     | 25%  | 24%  | 40%  | 32%  | 30%  | 31%  | 36%  | 36%  | 31%  |
| 23     | 27%  | 48%  | 44%  | 47%  | 47%  | 61%  | 51%  | 48%  | 58%  |
| 24     | 23%  | 44%  | 49%  | 43%  | 44%  | 37%  | 32%  | 55%  | 55%  |
| 2      |      | 94%  | 94%  | 95%  | 94%  | 96%  | 94%  | 95%  | 94%  |
| 4      | 94%  |      | 98%  | 97%  | 97%  | 97%  | 99%  | 98%  | 98%  |
| 5      | 94%  | 98%  |      | 96%  | 95%  | 97%  | 97%  | 97%  | 97%  |
| 6      | 95%  | 97%  | 96%  |      | 96%  | 96%  | 97%  | 97%  | 96%  |
| 12     | 94%  | 97%  | 95%  | 96%  |      | 97%  | 99%  | 99%  | 97%  |
| 15     | 96%  | 97%  | 97%  | 96%  | 97%  |      | 94%  | 98%  | 94%  |
| 16     | 94%  | 99%  | 97%  | 97%  | 99%  | 24%  |      | 98%  | 95%  |
| 19     | 95%  | 98%  | 97%  | 97%  | 99%  | 98%  | 98%  |      | 97%  |
| 22     | 94%  | 98%  | 97%  | 96%  | 97%  | 94%  | 95%  | 97%  |      |
| counts | 1406 | 6043 | 2713 | 3729 | 4299 | 3202 | 3561 | 3026 | 2722 | total, 5281 heterozygous SNPs and 3159 homozygous SNPs are detected (see methods), with a combined transition/transversion (Ti/Tv) ratio of 2.16, consistent with the typical value observed for humans. To see if these numbers are reasonable, they were compared with a study which reported a total of 1762541 heterozygous SNPs in the genome of Dr. Craig Venter (S. Levy et al., *PLoS Biol* 5, e254 (Sep. 4, 2007)). This suggests that about 35250 heterozygous sites on Chr19 could be expected for an individual. In our experiment about 15% of the positions on Chr19 are covered by at least 10 reads when aggregated across all tags (FIG. 3), so assuming that a minimum coverage of 10 reads is needed to make a SNP call, it was expected to detect 5287 heterozygous SNPs. Thus the number of heterozygous SNPs detected from the data presented here is in line with expectation. Of the 5281 heterozygous SNPs detected from data presented here, 4633 match to refSNP positions; and of the 3159 homozygous SNPs, 2709 match to refSNP positions. The higher than 85% validation by refSNP suggests that the SNP calling method is highly reliable and that most of the remaining 1098 SNPs not found in refSNP are novel and private SNPs in this individual. It is worth emphasizing that all the detected SNPs are completely phased relative to each other regardless of distance.

A significant portion of the heterozygous SNPs identified here, 2815 out of 5281 map to the transcription unit of 1185 RefSeq genes on Chr19. 281 of the heterozygous SNPs map to RefSeq exons, and 137 map to RefSeq coding regions. Among the 3150 homozygous SNPs identified here, 1438 map to 807 RefSeq transcription units, 150 map to RefSeq exons, and 72 map to RefSeq coding regions. 72 heterozygous SNPs and 34 homozygous SNPs result in non-synonymous change in RefSeq coding regions.

Finally, based on the insertion/deletion (indel) calling function in next_phred, 202 small indels of sizes 1, 2 or 3 bp were discovered and phased throughout Chr19.

Example 2

Isolation of Specific Genomic Regions

Figure 4:
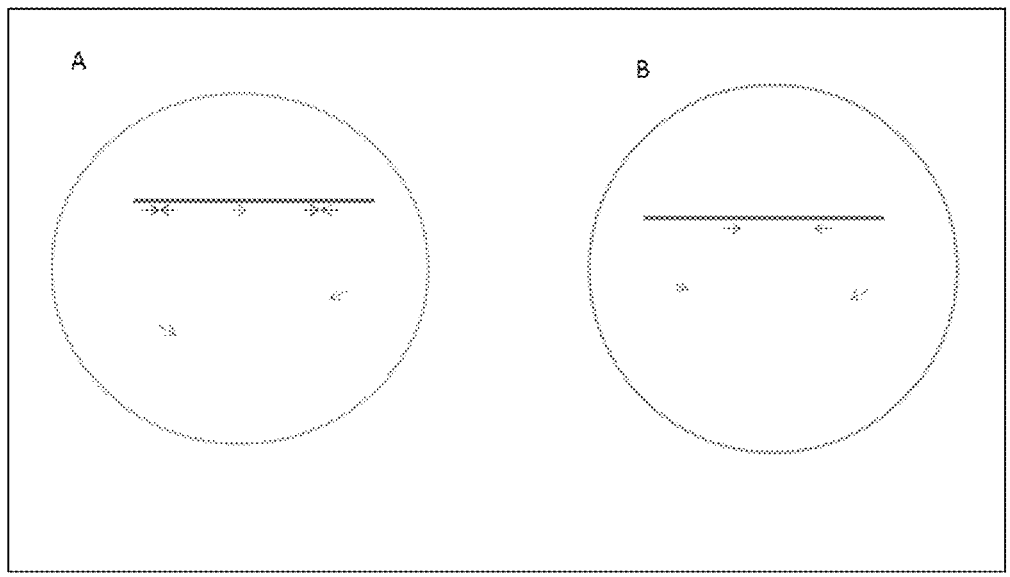
FIG. 4 depicts a schematic of an embodiment of a method provided herein.

Also provided herein is a method to efficiently isolate chromosomal fragments containing matches to a set of targeting sequences. In certain embodiments, the targeting sequences may be specific short sequences (for example, approximately 100 bp in size). These targeting sequences are designed to identify a genomic region of interest. For example, s may be a sequence in this set of targeting sequences. a and b may be labeled probes that specifically hybridize to non-overlapping sub-regions in s. The detectable label used to label a may contain a donor molecule and the detectable label used to label b may contain an accepter molecule, or vice versa, that provide a fluorescence resonance transfer (FRET) interaction. In certain cases, the chromosomes are fragmented to desired size range (e.g. about 1 megabase (mb), or about 2 mb, or about 4 mb, or about 8 mb, or about 12 mb, or about 18 mb, or about 25 mb, or about 30 mb, or about 50 mb, denatured and then hybridized to FRET probes corresponding to the targeting sequences. After a probe removal step, flow cytometry and sorting of the fragments may be performed. FIG. 4 shows the possible outcomes when a FACS droplet containing a fragment is interrogated by the laser at the illumination/detection zone. FIG. 4A shows that if the droplet contains matches to targeting sequences, the corresponding pair of FRET probes (red) will produce fluorescent signal when illuminated. FIG. 4 B shows that if the droplet does not contain such matches, then even if there is non-specific hybridization, the unpaired probes (grey) will not produce a signal.

Figure 5:
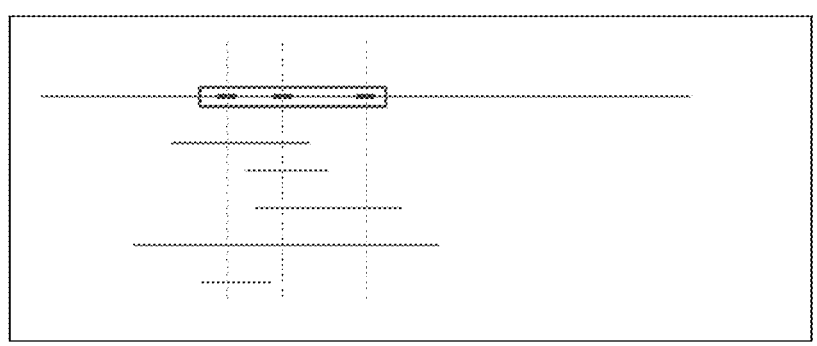
FIG. 5 shows the tiling of the fragments collected based on FRET signal.

Thus, based on the FRET signal, specifically those fragments that contain matches to the targeting sequences may be collected into the same container for unphased sequencing, or into separate containers each containing a single fragment, for phased sequencing as above FIG. 5 shows that the targeted genomic region will be tiled by the fragments from the FACS experiments. Fragments containing matches to the targeting sequences (red) are collected as described above. Together, these fragments provide sequence reads tiling the genomic region of interest.

The collected fragments are used to prepare sequencing libraries, and the resulting sequence reads can be analyzed to obtain the desired genetic information such as the existence of sequence variants, or to assemble the sequence of the region of interest independent of the reference genome sequence.

That which is claimed is:

1. A method comprising:
fragmenting a chromosome into chromosomal fragments;
contacting chromosomal fragments with a plurality of oligonucleotide probes, wherein the oligonucleotide probes contain a fluorescent signal, wherein the oligonucleotide probes bind to a nucleic acid comprising a nucleic acid sequence of interest,
isolating chromosomal fragments based on the fluorescent signal by using a fluorescence activated cell sorter, wherein the isolated chromosomal fragments associated with the fluorescent signal are separated from chromosomal fragments not associated with the fluorescent signal, wherein the isolating comprises collecting the isolated chromosomal fragments associated with the signal into separate containers each container containing no more than one chromosomal fragment;
sequencing the isolated fragments associated with the fluorescent signal to obtain sequence of the chromosomal fragment containing the nucleic acid sequence of interest.

2. The method of claim 1, wherein the chromosomal fragments are contacted with a one or more pairs of oligonucleotide probes, wherein each pair of oligonucleotide probes comprises a first probe and a second probe, wherein the first and second probes bind to a nucleic acid comprising the nucleic acid sequence of interest, the first and second probes comprising a donor molecule and an acceptor molecule, respectively, wherein the donor and acceptor molecules interact to produce a signal when first and second probes are bound to the nucleic acid.

3. The method of claim 1, wherein the isolating comprises collecting the isolated chromosomal fragments associated with the signal into a single container.

4. The method of claim 1, wherein the chromosomal fragments range in size from 1 megabase to 50 megabase.

5. The method of claim 1, wherein prior to said fragmenting step the method comprises:
separating a plurality of chromosomes of a target chromosome pair obtained from diploid cells of a subject into a plurality of single chromosomes present in individual containers, each container including at most a single chromosome, wherein the target chromosome pair comprises a maternally and a paternally inherited member.

6. The method of claim 5, wherein the sequencing the isolated chromosomal fragment associated with the fluorescent signal provides phased nucleic acid sequences for the single chromosomes;
grouping the plurality of single chromosomes into two clusters based on the phased nucleic acid sequences, wherein chromosomes within the same cluster have the same sequence at polymorphic sites; and optionally
correlating the phased nucleic acid sequences for the single chromosomes to a maternally or a paternally inherited member based on a characteristic known to be associated with a maternally or paternally inherited member.

7. The method of claim 1, wherein the fragmenting comprises enzymatically fragmenting the chromosome.

8. A method comprising:
separating a plurality of chromosomes of a target chromosome pair obtained from diploid cells of a subject into a plurality of single chromosomes present in individual containers, each container including at most a single chromosome, wherein the target chromosome pair comprises a maternally and a paternally inherited member;
fragmenting the plurality of single chromosomes present in the individual containers into chromosomal fragments;
contacting chromosomal fragments with one or more pairs of oligonucleotide probes, wherein each pair of oligonucleotide probes comprises a first probe and a second probe, wherein the first and second probes bind to a nucleic acid comprising a nucleic acid sequence of interest, the first and second probes comprising a donor molecule and an acceptor molecule, respectively, wherein the donor and acceptor molecules interact to produce a fluorescent signal when first and second probes are bound to the nucleic acid;
isolating chromosomal fragments based on the fluorescent signal by using a fluorescence activated cell sorter, wherein the isolated chromosomal fragments associated with the fluorescent signal are separated from chromosomal fragments not associated with the fluorescent signal;
sequencing the isolated chromosomal fragments associated with the fluorescent signal to provide phased nucleic acid sequences for the single chromosomes;
grouping the plurality of single chromosomes into two clusters based on the phased nucleic acid sequences, wherein chromosomes within the same cluster have the same sequence at polymorphic sites; and optionally correlating the phased nucleic acid sequences for the single chromosomes to a maternally or a paternally inherited member based on a characteristic known to be associated with a maternally or paternally inherited member.

9. The method of claim 8, wherein the isolating comprises collecting the isolated chromosomal fragments associated with the signal into a single container.

10. The method of claim 8, wherein the isolating comprises collecting the isolated chromosomal fragments associated with the signal into separate containers each container containing no more than one chromosomal fragment.

11. The method of claim 8, wherein the fragmenting comprises enzymatically fragmenting the chromosome.

12. The method of claim 8, wherein the chromosomal fragments range in size from 1 megabase to 50 megabase.

\* \* \* \* \*

SEQUENCE LISTING

```
<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 1
atggctttac gcacgatgaa tgtacgcgc                                      29

<210> SEQ ID NO 2
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 2
cgagatttac gcacgattaa tgtacgcgct                                     30
```

```
<210> SEQ ID NO 3
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 3
acactctttc cctacacgac gctcttccga tct                                33

<210> SEQ ID NO 4
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 4
ctcggcattc ctgctgaacc gctcttccga tct                                33
```